United States Patent
Gao et al.

(10) Patent No.: US 10,730,036 B2
(45) Date of Patent: Aug. 4, 2020

(54) METHOD FOR IN SITU HIGH ACTIVITY ODH CATALYST

(71) Applicant: NOVA Chemicals (International) S.A., Fribourg (CH)

(72) Inventors: Xiaoliang Gao, Calgary (CA); Vasily Simanzhenkov, Calgary (CA); Marie Barnes, Calgary (CA); David Sullivan, Calgary (CA); Hanna Drag, Calgary (CA); Yoonhee Kim, Calgary (CA); Perry de Wit, Calgary (CA)

(73) Assignee: NOVA Chemicals (International) S.A., Fribourg (CH)

( * ) Notice: Subject to any disclaimer, the term of this patent is extended or adjusted under 35 U.S.C. 154(b) by 8 days.

(21) Appl. No.: 16/261,917

(22) Filed: Jan. 30, 2019

(65) Prior Publication Data

US 2019/0240647 A1 Aug. 8, 2019

(30) Foreign Application Priority Data

Feb. 2, 2018 (CA) ..................................... 2993683

(51) Int. Cl.
| | | |
|---|---|---|
| *B01J 27/057* | (2006.01) | |
| *B01J 37/03* | (2006.01) | |
| *B01J 37/00* | (2006.01) | |
| *B01J 37/10* | (2006.01) | |
| *B01J 37/08* | (2006.01) | |
| *B01J 35/02* | (2006.01) | |
| *C07C 2/84* | (2006.01) | |
| *B01J 23/00* | (2006.01) | |
| *B01J 23/22* | (2006.01) | |
| *B01J 23/28* | (2006.01) | |
| *B01J 37/04* | (2006.01) | |
| *B01J 37/06* | (2006.01) | |
| *C07C 5/48* | (2006.01) | |
| *C07C 2/82* | (2006.01) | |
| *C07C 5/32* | (2006.01) | |

(52) U.S. Cl.
CPC ......... *B01J 27/0576* (2013.01); *B01J 23/002* (2013.01); *B01J 23/22* (2013.01); *B01J 23/28* (2013.01); *B01J 35/023* (2013.01); *B01J 37/0009* (2013.01); *B01J 37/0018* (2013.01); *B01J 37/0045* (2013.01); *B01J 37/0063* (2013.01); *B01J 37/03* (2013.01); *B01J 37/04* (2013.01); *B01J 37/06* (2013.01); *B01J 37/08* (2013.01); *B01J 37/088* (2013.01); *B01J 37/10* (2013.01); *C07C 2/84* (2013.01); *C07C 5/48* (2013.01); *B01J 2523/00* (2013.01); *C07C 2/82* (2013.01); *C07C 5/32* (2013.01); *C07C 2523/20* (2013.01); *C07C 2523/22* (2013.01); *C07C 2523/28* (2013.01); *C07C 2523/32* (2013.01)

(58) Field of Classification Search
CPC .... B01J 27/0576; B01J 37/03; B01J 37/0009; B01J 37/10; B01J 37/088; B01J 35/023; B01J 23/002; B01J 23/22; B01J 23/28; B01J 37/0018; B01J 37/0045; B01J 37/0063; B01J 37/04; B01J 37/06; B01J 37/08; C07C 2/84; C07C 5/48; C07C 5/32; C07C 2/82; C07C 2523/20; C07C 2523/22; C07C 2523/28; C07C 2523/32
See application file for complete search history.

(56) References Cited

U.S. PATENT DOCUMENTS

| | | | | |
|---|---|---|---|---|
| 7,319,179 | B2 * | 1/2008 | Lopez Nieto | .......... B01J 23/002 502/302 |
| 8,105,971 | B2 * | 1/2012 | Gaffney | ................. B01J 23/002 502/178 |
| 8,519,210 | B2 * | 8/2013 | Arnold | ...................... C07C 5/48 585/655 |
| 2014/0128653 | A1 * | 5/2014 | Bal | ........................ B01J 37/035 585/658 |

FOREIGN PATENT DOCUMENTS

| | | |
|---|---|---|
| IE | 1 2009 000 404 TS | 12/2010 |
| WO | 2009/022780 A1 | 2/2009 |

\* cited by examiner

*Primary Examiner* — Ali Z Fadhel
(74) *Attorney, Agent, or Firm* — Thomas J. Styslinger

(57) ABSTRACT

A process for preparing an oxidative dehydrogenation catalyst or oxidative dehydrogenation catalyst precursor that includes mixing solutions of molybdenum and tellurium at a pH from about 3.3 to 7.5; adjusting the pH of the resulting solution back to about 5 and adding $VOSO_4$ and adding a solution of $Nb_2O_5$ and oxalic acid and treating the resulting precursor slurry in a controlled pressure hydrothermal process to obtain the catalyst.

20 Claims, No Drawings

METHOD FOR IN SITU HIGH ACTIVITY ODH CATALYST

CROSS REFERENCE TO RELATED APPLICATIONS

This application claims the benefit of the earlier filing date of Canadian application serial number CA 2993683 filed on Feb. 2, 2018. The contents of Canadian application serial number CA 2993683 are incorporated herein by reference in their entirety.

TECHNICAL FIELD

The present disclosure relates to a process for the preparation of oxidative dehydrogenation catalyst (ODH) precursors in a single reactor that includes controlling the pH of the solution during the addition of the Mo, Te, and V components and then adding $Nb_2O_5$ and oxalic acid without separation of intermediate components. The resulting precursor, typically a slurry, is then subject to a controlled pressure hydrothermal process and the final catalyst may optionally be further treated with a peroxide. The process is highly reproducible.

SUMMARY

The present disclosure seeks to provide a process for preparing a catalyst including mixed oxides of MoVNbTe, the process includes the following steps:

i) forming an aqueous solution of ammonium heptamolybdate (tetrahydrate) and telluric acid in a molar ratio of Mo:Te 1:0.14 to 0.20, in some instances from 1:0.17, at a temperature from 30° C. to 85° C. and adjusting the pH of the solution to 6.5 to 8.5, for example from 7 to 8, or from 7.3 to 7.7—in some instances with a nitrogen-containing base to form soluble salts of the metals;

ii) stirring the pH adjusted solution for a time of not less than 15 minutes, in some instances from not less than 2 hours, in some instances not more than 4 hours;

iii) adjusting the pH of the resulting solution to from 4.5 to 5.5, for example from 4.8 to 5.2, or from 5.0 to 5.2 with an acid, for example sulfuric acid (0.01-18 M, typically 2-18 M) and stirring the resulting solution at a temperature of 80° C. until it is homogeneous, in some instances with a stirring time up to 30 minutes; in some circumstances, to maintain 80° C. temperature, a cooling device can be used to maintain temperature at 80° C.

iv) preparing an aqueous solution of vanadyl sulphate at a temperature from room temperature to 80° C. (for example, from 50° C. to 70° C. or from 55° C. to 65° C.);

v) mixing the solutions from steps i) and iv) together to provide a molar ratio of V:Mo from 1.00-1.67 to 1, in some cases from 1.45-1.55 to 1.00 vi) preparing a solution of $H_2C_2O_4$ and $Nb_2O_5xH_2O$ in a molar ratio from 5.0 to 6:0:1, in some instances 5.0-5.3:1;

vii) slowly (e.g., dropwise) adding the solution from step vi) to the solution of step v) to provide a molar ratio of Nb:Mo from 5.56-7.14:1 (e.g., from 6.20-6.40:1) to form a slurry; typically, the addition is at temperatures from 20° C. and 80° C. (e.g., from 20° C. to 30° C.).

vii) heating the resulting slurry in an autoclave under an inert gas, air, carbon dioxide, carbon monoxide and mixtures thereof at a pressure of not less than 1 psig and at a temperature from 140° C. to 190° C. for not less than 6 hours.

In some embodiments, the temperature for the hydrothermal treatment is from 140° C. to 180° C. In some embodiments, from 145° C. to 175° C. For example, from 160° C. to 165° C.

In some embodiments, the pressure in the autoclave is from 30 to 200 psig (e.g., from 206 kPag to 1375 kPag). In some embodiments, from 55 psig (380 kPag) to 170 psig (1170 kPag) above atmospheric pressure.

In some embodiments, the gaseous product species are vented from the reactor (autoclave).

In some embodiments, there is a condenser downstream of the autoclave outlet.

In some embodiments, the condenser is operated at a temperature above 0° C. and below reaction temperature.

In some embodiments, the pressure inside the autoclave is maintained above atmospheric pressure using one of the following: a liquid filled column, bubbler, or pressure regulating device.

In some embodiments, the time of the hydrothermal treatment is not less than 6 hours and in some cases 60 hours or more.

In some embodiments, the aqueous slurry includes Mo, V, Nb, and Te salts in a molar ratio of Mo 1; V 0.4 to 0.70; Nb 0.14 to 0.18; and Te 0.14 to 0.20.

In some embodiments, the heat-treated slurry from step vii) is treated with from 0.3-2.5 mL of a 30 wt. % solution of aqueous $H_2O_2$ per gram of catalyst precursor.

In some embodiments, the resulting pre-catalyst is separated from the aqueous phase and washed with (distilled) water and dried in an oven for not less than 6 hours at a temperature from 70° C. to 120° C.

In some embodiments, the dried precatalyst is ground, typically to a particle size less than 125 μm.

In some embodiments, the dried precatalyst is calcined in an inert atmosphere at a temperature from 200° C. to 650° C. for a time from 1 to 20 hours.

In some embodiments, the catalyst is ground to a particle size less than 125 microns and then re-dried in an oven at 90° C. for not less than 2 hours before being subjected to a calcination procedure.

In some embodiments, from 10 wt. % to 95 wt. %, from 25 wt. % to 80 wt. %, or from 30 wt. % to 45 wt. % of the catalyst is bound or agglomerated with from 5 wt. % to 90 wt. % (e.g., from 20 wt. % to 75 wt. % or from 55 wt. % to 70 wt. %) of a binder selected from acidic, basic, or neutral binder slurries of $TiO_2$, $ZrO_2Al_2O_3$, $AlO(OH)$, $Nb_2O_5$ and mixtures thereof provided that $ZrO_2$ is not used in combination with an aluminum containing binder.

In a further embodiment, there is provided a method for the oxidative dehydrogenation of a mixed feed including ethane and oxygen in a volume ratio from 70:30 to 95:5 and, optionally, one or more $C_{3-6}$ alkanes or alkenes and oxygenated species including CO and $CO_2$ at a temperature greater than 320° C. up to 385° C., a gas hourly space velocity of not less than 100 $hr^{-1}$, and a pressure from 0.8 to 7 atmospheres including passing the mixture over the above catalyst.

In some embodiments, the ODH process has a selectivity to ethylene of not less than 90%.

In some embodiments, the gas hourly space velocity of the ODH process is not less than 500 $hr^{-1}$ (e.g., not less than 1500 $hr^{-1}$). In some embodiments, the gas hourly space velocity of the ODH process is not less than 3000 $hr^{-1}$.

In some embodiments, the temperature of the ODH process is less than 375° C., preferably less than 360° C.

In some embodiments, the catalyst in the ODH process forms a fixed bed.

DETAILED DESCRIPTION

Numbers Ranges

Other than in the operating examples or where otherwise indicated, all numbers or expressions referring to quantities of ingredients, reaction conditions, etc. used in the specification and claims are to be understood as modified in all instances by the term "about". Accordingly, unless indicated to the contrary, the numerical parameters set forth in the following specification and attached claims are approximations that can vary depending upon the properties that the present disclosure desires to obtain. At the very least, and not as an attempt to limit the application of the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the invention are approximations, the numerical values set forth in the specific examples are reported as precisely as possible. Any numerical values, however, inherently contain certain errors necessarily resulting from the standard deviation found in their respective testing measurements.

Also, it should be understood that any numerical range recited herein is intended to include all sub-ranges subsumed therein. For example, a range of "1 to 10" is intended to include all sub-ranges between and including the recited minimum value of 1 and the recited maximum value of 10; that is, having a minimum value equal to or greater than 1 and a maximum value of equal to or less than 10. Because the disclosed numerical ranges are continuous, they include every value between the minimum and maximum values. Unless expressly indicated otherwise, the various numerical ranges specified in this application are approximations.

All compositional ranges expressed herein are limited in total to and do not exceed 100 percent (volume percent or weight percent) in practice. Where multiple components can be present in a composition, the sum of the maximum amounts of each component can exceed 100 percent, with the understanding that, and as those skilled in the art readily understand, the amounts of the components actually used will conform to the maximum of 100 percent.

In the specification, the phrase the temperature at which there is 25% conversion of ethane to ethylene is determined by plotting a graph of conversion to ethylene against temperature typically with data points below and above 25% conversion or the data is fit to an equation and the temperature at which there is a 25% conversion of ethane to ethylene is determined. In some instances, in the examples, the data was extrapolated to determine the temperature at which 25% conversion occurred.

In the specification, the phrase selectivity at 25% conversion is determined by plotting the selectivity as function of temperature or fit to an equation. Then having calculated the temperature at which 25% conversion occurs one can determine either from the graph or from the equation the selectivity at that temperature.

As used herein, non-antagonistic binder means a binder other than $Nb_2O_5$ which when incorporated into the agglomerated catalyst has less than a 5% antagonistic effect on the agglomerated catalysts. Some non-antagonistic binders include oxides of aluminum, titanium and zirconium. Silica oxides have an antagonistic effect on the agglomerated catalysts and the catalyst active sites.

The slurry (gel) has the following stoichiometric ratio: Mo1:V0.50-0.70:Te0.14-0.20:Nb0.14-0.18

The catalysts of the present disclosure include mixed oxides of Mo, V, Nb, and Te. The catalysts may be represented by the empirical formula:

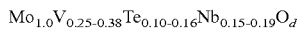

$$Mo_{1.0}V_{0.25-0.38}Te_{0.10-0.16}Nb_{0.15-0.19}O_d$$

where d is a number to satisfy the valence of the oxide.

The catalyst precursor may be prepared by the following steps:

i) Forming an aqueous solution of ammonium heptamolybdate (tetrahydrate) and telluric acid in a molar ratio of Mo:Te 1:0.14 to 0.20—in some instances from 1:0.16 to 1:0.18 (e.g., 1:0.17)—at a temperature from 30° C. to 85° C. and adjusting the pH of the solution to 6.5 to 8.5, (e.g., from 7 to 8 such as from 7.3 to 7.7), for example, with a nitrogen-containing base such as $NH_4OH$ to form water soluble salts of the metals.

ii) Stirring the pH adjusted solution for a time of not less than 15 minutes, in some instances from not less than 2, in some instances not more than 4 hours. For example, from 2.5 hours to 3.5 hours.

iii) Adjusting the pH of the resulting solution to from 4.5 to 5.5 (e.g., from 4.8 to 5.2 or from 5.0 to 5.2) with an acid, such as sulfuric acid (0.01-18 M, such as 2-18 M) and stirring the resulting solution at a temperature from 75° C. to 85° C. (e.g., 80° C.) until it is homogeneous—in some instances, with a stirring time up to 30 minutes. In some embodiments, to maintain the temperature, a cooling device can be used.

iv) Preparing a 0.30 to 0.50 molar (e.g., a 0.36 to 0.48 molar or a 0.40 to 0.45 molar) aqueous solution of vanadyl sulphate at a temperature from room temperature to 80° C. (e.g., from 50° C. to 70° C. or from 55° C. to 65° C.).

v) Mixing the solutions from steps iii) and iv) together to provide a molar ratio of V:Mo from 1.00-1.67 to 1.00 (e.g., from 1.45-1.55 to 1.00).

vi) Preparing a solution of $H_2C_2O_4$ and $Nb_2O_5xH_2O$ in a molar ratio from 3:1 to 6.5:1 (e.g., from 4.5:1 to 6.5:1 or 6:1).

vii) Slowly (e.g., dropwise) adding the solution from step vi) to the solution of step v) to provide molar ratio of Nb:Mo from 5.56-7.14:1 in some instances from 6.20-6.40:1. In some embodiments, the resulting mixture will be a slurry generally a purple/grey color.

vii) Heating the resulting slurry in an autoclave under an inert gas, air, carbon dioxide, carbon monoxide, or a mixture thereof at a temperature from 150° C. to 190° C. In some embodiments, for not less than 10 hours at a pressure generally up to 200 psig (1375 kPag).

The initial solution is prepared by dissolving ammonium heptamolybdate (tetrahydrate) $((NH_4)_6Mo_7O_{24}.4H_2O)$ in a suitable solvent, such as water. The water is typically at a room temperature (e.g., from 20 to 25° C.) and is stirred at medium speed (e.g., from 150 to 500 rpm, such as 250 to 350 rpm or 300 rpm) using a stirrer mechanical or magnetic. The initial solution may be from about 0.3 to 0.5 molar, such as from about 0.3 to 0.4 molar. The ammonium heptamolybdate (tetrahydrate) should dissolve in about 10 minutes forming a clear or turbid solution. A 0.2 to 0.3 molar solution of telluric acid is prepared in water. The solution should be clear before proceeding. The telluric acid solution is added to the ammonium heptamolybdate (tetrahydrate) dropwise at 0.20-0.50 L/min) using a dropper funnel or transfer lines. The resulting solution is clear and colorless. The resulting solution is heated to 80° C. The pH of the solution is measured. Generally, it is in the range from about 3.0 to 3.5, such as 3.2 to 3.4. The pH of the solution is adjusted to from 7.2 to 7.7, such as from 7.4 to 7.6. In some embodiments, pH of the solution is adjusted to 7 using a water-soluble base typically ammonium hydroxide. The resulting solution can be kept at 80° C. under low agitation for not less than 1 hour, typically from 1 to 6 hours, such as from 1 to 2 hours.

An aqueous solution of VOSO$_4$ is prepared by dissolving VOSO$_4$ in a water bath at a temperature from room temperature to 80° C. (e.g., from 50° C. to 70° C. such as such as from 55° C. to 65° C.). The solution having a molar concentration of V from 1.30 to 1.70 (e.g., from 1.36 to 1.55, such as from 1.50 to 1.55). The solution can be clear blue after not less than 30 or from 30 to 60 minutes of moderate stirring in the water bath. The solution of VOSO$_4$ can be added dropwise over a period of not less than 20 minutes—or from 20 to 60 minutes—to the solution of Mo and Te, which can be maintained at 80° C. to provide a molar ratio of V:Mo from 25:1 to 30:1, for example 27:1 to 38:1 or 34:1 to 36:1. The resulting solution was a clear light blue. The solution can be stirred under medium agitation. For example, the solution can be stirred from 200 to 400 rpm, from 250 to 350 rpm, or from 275 to 325 rpm while the solution cooled to room temperature.

In some embodiments, the vanadyl sulfate solution may be buffered with a glycine/sulfuric acid buffer. Other buffers would be known to those skilled in the art.

An aqueous solution of C$_2$H$_2$O$_4$ and Nb$_2$O$_5$xH$_2$O in a molar ratio from 3:1 to 10:1, (e.g., from 4:1 to 7:1, such as 6:1) can be prepared at 60° C. to 70° C. with moderate stirring at 100 to 300 rpm for from 16 to 30 hours (e.g., from 22 to 26 hours). This can result in a turbid solution of niobium oxalate. The niobium oxalate solution can be added dropwise to the solution of MoTeVO$_x$ with stirring at a rate from 700 to 1400 rpm, (e.g., from 900 to 1300 rpm) to provide a molar ratio of Nb:V from 0.85:1 to 0.95:1, (e.g., from 0.89:1 to 0.91:1). A precipitate can form and the resulting slurry can be purple/gray.

The resulting slurry can be transferred to a pressurized reactor (e.g., a Parr reactor or an autoclave) under an inert atmosphere and heated at a temperature from 140° C. to 190° C. (e.g., from 140° C. to 180° C. or from 145° C. to 175° C.) for not less than 6 hours (e.g., not less than 12 hours), and, in some embodiments, up to 30 hours, or more.

The pressure in the reactor (Parr reactor or autoclave) may range from 1 to 200 psig (6.89 kPag to 1375 kPag).

In some embodiments, the pressure in the pressurized reactor is adjusted and maintained from 30 to 200 psig (206 kPag to 1375 kPag). In some embodiments, the pressure in the pressurized reactor is adjusted and maintained from 55 psig (380 kPag) to 170 psig (1170 kPag) above atmospheric pressure.

In some embodiments, the pressure in the reactor (autoclave) may be up to about 10 psig (68.9 kPag), preferably from 1 to 8 psig (6.89 kPag to 55.1 kPag), in some embodiments less than 5 psig (34.4 kPag) above atmospheric pressure.

The pressures in the reactor can be maintained using a pressure relief valve. At lower pressures the pressure may be maintained by passing the off gas through a column of a fluid such as water or a dense fluid (e.g., mercury). Optionally, there may be a condenser upstream of the reactor outlet. If present, the condenser is operated at a temperature above 0° C. and below reaction temperature. Gaseous product species can be vented from the reactor as described above.

The reactor can be allowed to cool to room temperature, typically overnight. The reactor contents can be filtered using a Buchner filter and washed with (distilled) water or an aqueous oxalic acid solution and dried in an oven for not less than 6 hours at a temperature from 70° C. to 120° C. The dried precatalyst can be ground, to a size less than 125 μm and calcined in an inert atmosphere such as nitrogen, at a temperature from 200° C. to 650° C. for a time from 1 to 20 hours.

In some embodiments, the precatalyst is separated from the aqueous phase, typically by filtration or evaporation, and washed with (distilled or deionized) water or a (dilute) aqueous oxalic acid solution and dried in an oven for not less than 6 hours at a temperature from 70° C. to 120° C. The precatalyst may be dried in an atmosphere of one or more inert gases or the atmosphere may contain oxygen (e.g., air). In some embodiments, the dried precatalyst may be ground using mechanical means (e.g., a ball or roller mill) or the dried precatalyst can be subject to cryogenic grinding. The dried and ground precatalyst may, in some instances, be subject to sieving through a small particle size sieve to obtain a fraction having a particle size less than 250 microns, such as less than 125 microns.

In some embodiments, the product from the hydrothermal treatment is treated with from 0.3-2.5 mL of a 30 wt. % solution of aqueous H$_2$O$_2$ per gram of catalyst precursor.

Generally, the catalyst precursor (i.e., prior to calcining) has the formula:

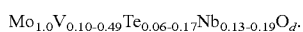
$$Mo_{1.0}V_{0.10-0.49}Te_{0.06-0.17}Nb_{0.13-0.19}O_d.$$

The calcined catalyst has the formula:

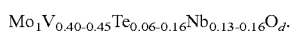
$$Mo_1V_{0.40-0.45}Te_{0.06-0.16}Nb_{0.13-0.16}O_d.$$

If the precatalyst is treated hydrothermally at pressures of less than about 10 psig (68.9 kPag), it has the formula:

$$Mo_{1.0}V_{0.17-0.20}Te_{0.06-0.07}Nb_{0.19-0.20}O_d$$

If the hydrothermal treatment is conducted at pressures greater than 30 psig ((206 kPag), the precatalyst has the formula:

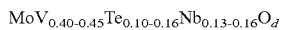
$$MoV_{0.40-0.45}Te_{0.10-0.16}Nb_{0.13-0.16}O_d$$

The calcined catalyst has an XRD having a main peak at 2 Φ at 22° having a half height peak width from 19 to 21 and broad secondary peak at 28° having a half width from 25 to 33°.

In some embodiments, from 10 wt. % to 95 wt. %, 25 wt. % to 80 wt. %, or from 30 wt. % to 45, wt. % of the catalyst is bound or agglomerated with from 5 wt. % to 90 wt. %, 20 wt. % to 75, or from 55 wt. % to 70 wt. % of a binder selected from the group consisting of acidic, basic, or neutral binder slurries of TiO$_2$, ZrO$_2$Al$_2$O$_3$, AlO(OH), Nb$_2$O$_5$ and mixtures thereof provided that ZrO$_2$ is not used in combination with an aluminum containing binder.

The catalyst may be used for the oxidative dehydrogenation of a mixed feed including ethane and oxygen in a volume ratio from 70:30 to 95:5 and optionally one or more C$_{3-6}$ alkanes or alkenes and optionally a further oxygenated species including CO and CO$_2$ at a temperature less than 385° C., a gas hourly space velocity of not less than 100 hr$^{-1}$, and a pressure from 0.8 to 7 atmospheres including passing the mixture over the above catalyst. The ODH process can have a selectivity to ethylene of not less than 90%. The gas hourly space velocity of the ODH process is not less than 500 hr$^{-1}$ such as not less than 1500 hr$^{-1}$ or 3000 hr$^{-1}$. The temperature of the ODH process can be less than 375° C., such as less than 360° C.

In some embodiments, the catalyst in the ODH process forms a fixed bed.

The present disclosure also provides a process for preparing a catalyst including mixed oxides of MoVNbTe that includes the following steps:

i) forming an aqueous solution of ammonium heptamolybdate (tetrahydrate) and telluric acid in a molar ratio of Mo:Te 1:0.14 to 1:0.20, at a temperature from 30° C. to 85° C. and adjusting the pH of the solution to 6.5 to 8.5, with a nitrogen-containing base to form soluble salts of the metals;

ii) stirring the pH adjusted solution for a time of not less than 15 minutes;

iii) adjusting the pH of the resulting solution to from 4.5 to 5.5, with an acid, and stirring the resulting solution at a temperature of 75° C. to 85° C. until it is homogeneous;

iv) preparing an aqueous 0.30 to 0.50 molar solution of vanadyl sulphate at a temperature from room temperature to 80° C.;

v) mixing the solutions from steps i) and iv) together to provide a molar ratio of V:Mo from 25:1 to 30:1;

vi) preparing a solution of $H_2C_2O_4$ and $Nb_2O_5xH_2O$ in a molar ratio from 3:1 to 6.5:1;

vii) slowly adding the solution from step vi) to the solution of step v) to provide molar ratio of Mo:Nb from 5.56:1 to 7.14:1 to form a slurry; and viii) heating the resulting slurry in an autoclave under an inert gas, air, carbon dioxide, carbon monoxide and mixtures thereof at a pressure of not less than 1 psig at a temperature from 140° C. to 190° C. for not less than 6 hours.

In some embodiments, the present disclosure provides in combination with one or more other embodiments a process wherein the temperature for the hydrothermal treatment is from 140° C.-180° C.

In some embodiments, the present disclosure provides in combination with one or more other embodiments a process wherein the pressure in the autoclave is from 1 to 200 psig (206 kPag to 1375 kPag), above atmospheric pressure.

In some embodiments, the present disclosure provides in combination with one or more other embodiments a process wherein the gaseous product species are vented from the reactor.

In some embodiments, the present disclosure provides in combination with one or more other embodiments a process wherein there is a condenser upstream of the autoclave outlet.

In some embodiments, the present disclosure provides in combination with one or more other embodiments a process wherein the condenser is operated at a temperature above 0° C. and below reaction temperature.

In some embodiments, the present disclosure provides in combination with one or more other embodiments a process wherein the pressure inside the autoclave is maintained above atmospheric using a liquid filled column or bubbler or pressure regulating device In some embodiments, the present disclosure provides in combination with one or more other embodiments a process wherein the time of the hydrothermal treatment is from 6 to 60 hours.

In some embodiments, the present disclosure provides in combination with one or more other embodiments a process wherein the aqueous slurry fed to the autoclave comprises Mo, V, Nb and Te salts in a molar ratio; Mo 1; V 0.40 to 0.70; Nb 0.14 to 0.18; and Te 0.14 to 0.20.

In some embodiments, the present disclosure provides in combination with one or more other embodiments a process wherein heat-treated slurry from step viii) is treated with from 0.3-2.5 mL of a 30 wt. % solution of aqueous $H_2O_2$ per gram of catalyst precursor.

In some embodiments, the present disclosure provides in combination with one or more other embodiments a process wherein the precatalyst from step viii) is separated from the aqueous phase and washed with (distilled) water or an aqueous oxalic acid solution and mixtures thereof and dried in an oven for not less than 6 hours at a temperature from 70° C. to 120° C.

In some embodiments, the present disclosure provides in combination with one or more other embodiments a process wherein the dried precatalyst is ground, to a particle size less than 125 μm. The dried catalyst may also be pre-dried in a 90° C. oven for no less than 6 hours before calcination.

In some embodiments, the present disclosure provides in combination with one or more other embodiments a process wherein the dried precatalyst is calcined in an inert atmosphere at a temperature from 200° C. to 650° C. for a time from 1 to 20 hours.

In some embodiments, the present disclosure provides in combination with one or more other embodiments a process where the calcined material (catalyst) is mixed with 0.1 wt. % to 10 wt. % (relative to catalyst) $Nb_2O_5xH_2O$ at 90° C. in water then dried at 300° C. in air.

In some embodiments, the present disclosure provides in combination with one or more other embodiments a process wherein from 10 wt. % to 95 wt. % of the catalyst is bound or agglomerated with from 5 wt. % to 90 wt % of a binder selected from acidic, basic, or neutral binder slurries of $TiO_2$, $ZrO_2Al_2O_3$, AlO(OH), $Nb_2O_5$ and mixtures thereof provided that $ZrO_2$ is not used in combination with an aluminum containing binder.

In some embodiments, the present disclosure provides in combination with one or more other embodiments a method for the oxidative dehydrogenation of a mixed feed including ethane and oxygen in a volume ratio from 70:30 to 95:5 and optionally one or more $C_{3-6}$ alkanes or alkenes and oxygenated species including CO and $CO_2$ at a temperature greater than 320° C. up to than 385° C., a gas hourly space velocity of not less than 100 $hr^{-1}$, and a pressure from 0.8 to 7 atmospheres including passing said mixture over a catalyst prepared according to any previous embodiment or combinations thereof.

In some embodiments, the present disclosure provides in combination with one or more other embodiments a method for the oxidative dehydrogenation of a lower $C_{2-4}$ paraffin typically ethane to the corresponding olefin(s) having a selectivity to olefin typically ethylene of not less than 90% at a target ethane conversion of greater than 25-35%, such as 35%.

In some embodiments, the present disclosure provides in combination with one or more other embodiments a method for the oxidative dehydrogenation of a lower $C_{2-4}$ paraffin typically ethane to the corresponding olefin(s) wherein the gas hourly space velocity of the ODH process is not less than 500 $hr^{-1}$.

In some embodiments, the present disclosure provides in combination with one or more other embodiments a method for the oxidative dehydrogenation of a lower $C_{2-4}$ paraffin typically ethane to the corresponding olefin(s) wherein the temperature is less than 375° C.

In some embodiments, the present disclosure provides in combination with one or more other embodiments a method for the oxidative dehydrogenation of a lower $C_{2-4}$ paraffin typically ethane to the corresponding olefin(s) wherein the catalyst in the ODH process forms a fixed bed.

EXAMPLES

The following comparative example and examples of preparations in accordance with the present disclosure illustrate the invention.

Comparative Example. Synthesis Reaction with No pH Adjustments

TABLE 1

| Reagent/Solvent | Amount required (g) | Amount Used (g) | Lot number |
|---|---|---|---|
| $Nb_2O_5 \cdot H_2O$ | 11.30 | 11.3792 | |
| $(NH_4)_6Mo_7O_{24} \cdot 4H_2O$ | 84.30 | 84.3011 | |
| $Te(OH)_6$ | 18.30 | 18.3022 | BCBF3366V |
| $VOSO_4 \cdot 3.46H_2O$ | 70.30 | 70.3022 | |
| $H_2C_2O_4$ | 19.00 | 19.0041 | |

1.37 g of $Nb_2O_5 \cdot XH_2O$ was charged into a 250 mL RBF with a magnetic stir bar and 130 mL of distilled $H_2O$ ($dH_2O$) forming a milky white suspension. While this mixture was stirring 19.00 g of oxalic acid was charged into the 250 mL RBF. This mixture was left to stir overnight at 65° C. and left to stir for 24 h (using a silicon oil bath) stirring at 300 rpm. The mixture was an opaque milky color. After 24 h of stirring at 65° C. the solution was a turbid and colorless solution. To a 2 neck 500 mL RBF was charged 84.3011 g of $(NH_4)_6MoO_{24} \cdot 4H_2O$ and 300 mL of $dH_2O$. This mixture was stirred to dissolve, dissolution time was 7 minutes at 400 rpm. To a 300 mL beaker was charged 18.3022 g of $Te(OH)_6$ and 100 mL of $dH_2O$ and stirred to dissolve at room temperature at 400 rpm. The dissolution time for this mixture is 5 minutes. The now clear and colorless solution of telluric acid was charged dropwise into the clear and colorless $(NH_4)_6Mo_7O_{24} \cdot 4H_2O$ solution using a dropper funnel, the addition time was 15 minutes and the resulting pH was 3.0. The solution temperature was increased to 80° C. using an oil bath, heating time to reach 80° C. was 30 minutes. 70.31 g of $VOSO_4$ was charged into a 250 mL beaker along with 100 mL of $dH_2O$. This mixture was stirred to dissolve in a 60° C. water bath, dissolution time was 30 minutes. The now clear blue solution was charged dropwise to the 60° C. MoTe solution from the previous step dropwise using an addition funnel, addition time was 20 minutes. The solution turns from a clear colorless solution to a dark purple/brown colored slurry. The pH of the resulting solution was 2.5 at 80° C. This slurry was cooled to room temperature, while stirring at 500 rpm the cool down time was approximately 1 hr. After the slurry had completely cooled to RT the Nb oxalate solution that was prepared previously and then held for later use was charged dropwise into the 2 L RBF using an addition funnel, the previously thin slurry became thick after the addition on Nb and resulted in a grey/purple thick slurry. The addition time for the Niobium Oxalate was 20 minutes. The slurry was transferred to a 2 L PARR reactor glass liner, which was placed inside the 2 L PARR reactor. The sealed PARR reactor was evacuated and backfilled 10× with nitrogen and vacuum, leaving 15 psi of nitrogen in the PARR reactor. The reactor was attached to the condenser/back pressure regulator set-up with the overhead agitator stand. The sealed reactor was left to stir overnight at room temperature. The following day the 15 psi left in the PARR reactor was vented through the condenser and back pressure regulator setup. The heater for the PARR reactor was set to 185° C., the inside thermowell target temperature was 175° C. After 6 h the heater to the PARR reactor was turned off and the reactor was left to cool overnight. The following day the purple slurry was filtered through 4× Whatmann #4 filter papers. Filtration took 18 hrs. The filtered powder was dried at 90° C. overnight.

Example 1: In Situ Preparation of Catalyst with pH Adjustments

Addition of Materials In Situ.

TABLE 2

| Reagent/Solvent | Amount Required | Amount used |
|---|---|---|
| $(NH_4)_6Mo_7O_{24} \cdot H_2O$ | 84.3 g | 84.36 g |
| $Te(OH)_6$ | 18.30 g | 18.34 g |
| $NH_4OH$ | 50 mL | 46 mL |
| $H_2SO_4$ (2M) | 80 mL | 79 mL |
| $Nb_2O_5xH_2O$ | 11.30 g | 11.37 g |
| of $H_2C_2O_4$ | 19.0 g | 19.09 g |
| $VOSO_4$ | 70.30 g | 70.31 g |
| Distilled $H_2O$ (Mo) | 300 mL | 300 mL |
| Distilled $H_2O$ (Te) | 100 mL | 100 mL |
| Distilled $H_2O$ (V) | 100 mL | 100 mL |
| Distilled $H_2O$ (Nb) | 127 g | 127 g |

To a 2 neck round bottom flask (RBF) was charge 84.29 g of $(NH_4)_6Mo_7O_{24} \cdot 4H_2O$. To this 2 L two neck RBF was charge 300 mL of distilled water.

The mixture was left to stir to dissolve, approximately 5 minutes to fully dissolve. To a 300 mL beaker was charged 18.29 g of $Te(OH)_6$. To this beaker charge 100 mL of distilled water. This salt/water mixture was stirred to dissolve in the distilled water at room temperature. Dissolution time was 8 to 10 minutes. The now clear and colorless solution of $Te(OH)_6$ is charged dropwise to the solution of $(NH_4)_6Mo_7O_{24}$ through a dropper funnel. Addition time was 10 to 12 minutes.

A pH probe was calibrated to both a pH of 7 and a pH of 4. The pH probe was affixed to one of the two inlets of the two neck round bottom flask. The temperature of the solution was increased to 80° C. The pH was monitored until the temperature reached 80° C. The pH of solution was about 3.3 at 80° C. The pH of the solution was adjusted from 3.3 to 7.5 using $NH_4OH$ using a dropper funnel and starting with at least 45 mL of $NH_4OH$. Approximately 38-40 mL of $NH_4OH$ was required to adjust the pH. The pH adjusted solution was agitated at 80° C. for 3 hrs. To a beaker was charged 70.32 g of $VOSO_4$ and 100 mL of distilled water. This mixture was stirred to dissolve in a 60° C. water bath. Agitated the mixture for 30 minutes. The result was a clear blue solution. This solution was held for later use. The pH probe was recalibrated to pH 7 and pH 4 respectively. The pH meter was affixed to the 2 neck round bottom flask. The temperature was slowly increased while monitoring the pH as it approached 80° C.

TABLE 3

| pH | Temperature (° C.) |
|---|---|
| 2.87 | 24.8 |
| 2.88 | 30.8 |
| 2.89 | 35.0 |
| 2.90 | 40.0 |
| 2.90 | 45.0 |
| 2.90 | 50.0 |
| 3.04 | 70.0 |
| 3.07 | 75.0 |
| 3.11 | 80.0 |

Once the solution mixture reached 80.0° C. the pH was measured at 3.11. 50 mL of $NH_4OH$ was charged into a 250 mL addition funnel to the catalyst mixture at 80° C. The pH was slowly adjusted dropwise using an addition funnel.

TABLE 4

| pH | Volume of NH₄OH charged (mL) |
|---|---|
| 3.11 | 0 |
| 3.16 | 3 |
| 3.35 | 5 |
| 4.27 | 10 |
| 6.42 | 15 |
| 6.84 | 20 |
| 7.05 | 25 |
| 7.18 | 30 |
| 7.29 | 35 |
| 7.39 | 40 |
| 7.5 | 47 |

The pH probe was removed and the solution was left to stir at 80° C. for 3 hours. To a separate 300 mL beaker was charged 100 mL of distilled water. This beaker was placed into a 60° C. water bath and stirred to dissolve in the warm water bath. After 30 minutes, the solution became clear and blue in color, this solution was held at 60° C. for later use. The pH adjusted MoTe clear colorless solution was adjusted back to 5.01 at 80° C. using sulfuric acid. 100 mL of sulfuric acid was charged into a 250 mL addition funnel. The pH of the solution was adjusted dropwise using this addition funnel.

TABLE 5

| pH | Amount of sulfuric acid added (mL) |
|---|---|
| 7.5 | 0 |
| 7.33 | 5 |
| 7.29 | 10 |
| 7.23 | 15 |
| 7.18 | 20 |
| 7.13 | 25 |
| 7.07 | 30 |
| 7.02 | 35 |
| 6.94 | 40 |
| 6.87 | 45 |
| 6.80 | 50 |
| 6.65 | 55 |
| 6.53 | 60 |
| 6.30 | 65 |
| 5.73 | 70 |
| 5.30 | 75 |
| 5.01 | 79 |

79 mL of sulfuric acid was required to adjust the pH of the solution to 5.01. The solution remained clear and colorless. The VOSO₄ clear blue solution that was being held at 60° C. was charged into a 250 mL dropper funnel and added dropwise into the 2 L RBF over 20 minutes at 80° C. 11.37 g of Nb₂O₅xH₂O was weighed into a 250 mL RBF; approx. 127 mL of distilled H₂O and a magnetic stirbar was added to the RBF. While stirring, 19.09 g of H₂C₂O₄ was added to the RBF. The RBF was put into an oil bath and heated to approx. 65° C. for approx. 24 hours. The MoTeVO$_x$ containing solution was left to stir 300 rpm for 30 minutes while the temperature was reduced to room temperature. After the clear and colorless MoTeVO$_x$ containing solution had returned to room temperature, the niobium oxalate solution (a turbid solution) that was set aside was charged into a 500 mL addition funnel. This solution was charged dropwise to the MoTeVO$_x$ containing solution via the addition funnel. The stir rate was increased to 1100 rpm. Precipitate began to form during this addition. The purple/grey slurry was transferred to a 2 L PARR reactor glass liner. The PARR reactor was sealed, evacuated and back filled 10 times with 15 psi N₂. PARR reactor was left under 15 psi nitrogen, insulated and connected to a backpressure regulator set-up stirring at 300 rpm. The reactor was left to stir sealed overnight.

Hydrothermal treatment. The N₂ (g) left in the PARR reactor was used to purge the set up. During the purging the backpressure regulator was dialed down to 160 psi. The PARR reactor was left stirring at 300 rpm. PARR reactor set up was heated using a heat controller

TABLE 6

| Temperature of heating jacket (° C.) | Temperature of Thermowell (° C.) | Pressure (psi) |
|---|---|---|
| 182 | 92 | |
| 185 | 150 | 150 |
| 185 | 160 | 160 |
| 185 | 172 | 160 |

The ramp rate required for reactor to reach temperature was 10 minutes. The ΔT between heating jacket and thermowell was 7° C. The PARR reactor was stirred (300 rpm) at this temperature (185° C. jacket and 172° C.) for 6 hours. The PARR reactor was left to cool overnight. The PARR reactor contents were filtered using a Buchner filtration apparatus and external vacuum set up. Approximately 500 mL of distilled water was used to rinse the filter cake. At this point the filtrate ran clear Example 2. Synthesis of Catalyst Performed In Situ While Decreasing the Temperature Addition of Materials In Situ.

TABLE 7

| Reagent/Solvent | Amount Required | Amount used |
|---|---|---|
| (NH₄)₆Mo₇O₂₄•H₂O | 84.3 g | 84.36 g |
| Te(OH)₆ | 18.30 g | 18.34 g |
| NH₄OH | 50 mL | 46 mL |
| H₂SO₄ (2M) | 80 mL | 79 mL |
| Nb₂O₅xH₂O | 11.30 g | 11.37 g |
| of H₂C₂O₄ | 19.0 g | 19.09 g |
| VOSO₄ | 70.30 g | 70.31 g |
| Distilled H₂O (Mo) | 300 mL | 300 mL |
| Distilled H₂O (Te) | 100 mL | 100 mL |
| Distilled H₂O (V) | 100 mL | 100 mL |
| Distilled H₂O (Nb) | 127 g | 127 g |

To a 2 neck round bottom flask (RBF) was charge 84.29 g of (NH₄)₆Mo₇O₂₄.4H₂O. To this 2 L two neck RBF was charge 300 mL of distilled water. The mixture was left to stir to dissolve, approximately 5 minutes to fully dissolve. To a 300 mL beaker was charged 18.29 g of Te(OH)₆. To this beaker charge 100 mL of distilled water. This salt/water mixture was stirred to dissolve in the distilled water at room temperature. The dissolution time was 8 to 10 minutes. The now clear and colorless solution of Te(OH)₆ is charged dropwise to the solution of (NH₄)₆Mo₇O₂₄ through a dropper funnel. Addition time was 10 to 12 minutes.

A pH probe was calibrated to both a pH of 7 and a pH of 4. The pH probe was affixed to one of the two inlets of the two neck round bottom flask. The temperature of the solution was increased to 80° C. The pH was monitored until the temperature reaches 80° C. The pH of solution was about 3.3 at 80° C. The pH of the solution was adjusted from 3.3 to 7.5 using NH₄OH using a dropper funnel and starting with at least 45 mL of NH$_4$OH. Approximately 38-40 mL of NH$_4$OH was required to adjust the pH. The pH adjusted solution was agitated at 80° C. for 3 hours. To a beaker was charged 70.32 g of VOSO$_4$ and 100 mL of distilled water. This mixture was stirred to dissolve in a 60° C. water bath. Agitate the mixture for 30 minutes. The result was be a clear blue solution. This solution was held for later use. The pH probe was recalibrated to pH 7 and pH 4 respectively.

The pH meter was affixed to the 2 neck round bottom flask. The temperature was slowly increased while monitoring the pH as it approached 80° C.

TABLE 8

| pH | Temperature (° C.) |
|---|---|
| 2.87 | 24.8 |
| 2.88 | 30.8 |
| 2.89 | 35.0 |
| 2.90 | 40.0 |
| 2.90 | 45.0 |
| 2.90 | 50.0 |
| 3.04 | 70.0 |
| 3.07 | 75.0 |
| 3.11 | 80.0 |

Once the solution mixture reached 80.0° C. the pH was measured at 3.11. 50 mL of NH$_4$OH was charged into a 250 mL addition funnel to the catalyst mixture at 80° C. The pH was slowly adjusted dropwise using an addition funnel.

TABLE 9

| pH | Volume of NH$_4$OH charged (mL) |
|---|---|
| 3.11 | 0 |
| 3.16 | 3 |
| 3.35 | 5 |
| 4.27 | 10 |
| 6.42 | 15 |
| 6.84 | 20 |
| 7.05 | 25 |
| 7.18 | 30 |
| 7.29 | 35 |
| 7.39 | 40 |
| 7.5 | 47 |

The pH probe was removed and the solution was left to stir at 80° C. for 3 hours. To a separate 300 mL beaker was charged 100 mL of distilled water. This beaker was placed into a 60° C. water bath and stirred to dissolve in the warm water bath. After 30 minutes the solution became clear and blue in color, this solution was held at 60° C. for later use. The pH adjusted MoTe clear colorless solution was adjusted back to 5.01 at 80° C. using sulphuric acid. 100 mL of sulphuric acid was charged into a 250 mL addition funnel. The pH of the solution was adjusted dropwise using this addition funnel.

TABLE 10

| pH | Amount of sulfuric acid added (mL) |
|---|---|
| 7.5 | 0 |
| 7.33 | 5 |
| 7.29 | 10 |
| 7.23 | 15 |
| 7.18 | 20 |
| 7.13 | 25 |
| 7.07 | 30 |

TABLE 10-continued

| pH | Amount of sulfuric acid added (mL) |
|---|---|
| 7.02 | 35 |
| 6.94 | 40 |
| 6.87 | 45 |
| 6.80 | 50 |
| 6.65 | 55 |
| 6.53 | 60 |
| 6.30 | 65 |
| 5.73 | 70 |
| 5.30 | 75 |
| 5.01 | 79 |

79 mL of sulfuric acid was required to adjust the pH of the solution to 5.01. The solution remained clear and colorless. The VOSO$_4$ clear blue solution that was being held at 60° C. was charged into a 250 mL dropper funnel and added dropwise into the 2 L RBF over 20 minutes at 80° C. 11.37 g of Nb$_2$O$_5$xH$_2$O was weighed into a 250 mL RBF; approx. 127 mL of distilled H$_2$O and a magnetic stirbar was added to the RBF. While stirring, 19.09 g of H$_2$C$_2$O$_4$ was added to the RBF. The RBF was put into an oil bath and heated to approx. 65° C. for approx. 24 hours. The MoTeVO$_x$ containing solution was left to stir 300 rpm for 30 minutes while the temperature was reduced to room temperature. After the clear and colorless MoTeVO$_x$ containing solution had returned to room temperature the Niobium Oxalate solution (a turbid solution) that was set aside was charged into a 500 mL addition funnel. This solution was charged dropwise to the MoTeVO$_x$ containing solution via the addition funnel. The stir rate was increased to 1100 rpm. Precipitate began to form during this addition. The purple/grey slurry was transferred to a 2 L PARR reactor glass liner.

The PARR reactor was sealed, evacuated and back filled 10 times with 15 psi N$_2$. PARR reactor was left under 15 psi nitrogen, insulated and connected to a backpressure regulator set-up stirring at 300 rpm. The reactor was left to stir sealed overnight.

Hydrothermal treatment. The N$_2$ (g) left in the PARR reactor was used to purge the set up. During the purging the backpressure regulator was dialed down to 160 psi. The PARR reactor was left stirring at 300 rpm. PARR reactor set up was heated using a heat controller. As the PARR reactor was heated up the pressure was dialed down to 100 psi.

TABLE 11

| Temperature of heating jacket (° C.) | Temperature of Thermowell (° C.) | Pressure (psi) |
|---|---|---|
| 157 | 92 | 30 |
| 157 | 150 | 55 |

Ramp rate required for reactor to reach temperature was 10 minutes. The ΔT between heating jacket and thermowell was 7° C. The PARR reactor was stirred (300 rpm) at this temperature (157° C. jacket and 120° C.) overnight. The PARR reactor was left to cool overnight. The PARR reactor contents were filtered using a Buchner filtration apparatus and external vacuum set up. Approximately 500 mL of distilled water was used to rinse the filter cake. At this point the filtrate ran clear.

The catalyst samples were tested for the dehydrogenation of ethane to ethylene. The catalyst samples of were loaded into a fixe bed reactor and ethane was passed through the sample. The activity at 25% conversion and selectivity at 25% conversion were recorded for each sample.

TABLE 12

| | Catalyst activities: | |
| --- | --- | --- |
| Catalyst code | Activity at 25% conversion (° C.) | Selectivity at 25% conversion (%) |
| Example 1 | 366.75 | 97.21 |
| Example 2 | 367.50 | 96.30 |
| Comparative Example | 396.00 | 96 |

The Examples show that catalysts prepared using the pH adjustment as described above have a 25% conversion at lower temperatures than the catalyst prepared without the pH adjustment (i.e. the catalysts are more reactive). Also, the catalysts prepared using the pH adjustment as described above have a slightly higher conversion to ethylene at 25% conversion.

What is claimed is:

1. A process for preparing a catalyst comprising mixed oxides of MoVNbTe comprising the following steps:
   i) forming an aqueous solution of ammonium heptamolybdate (tetrahydrate) and telluric acid in a molar ratio of Mo:Te 1:0.14 to 1:0.20, at a temperature from 30° C. to 85° C. and adjusting the pH of the solution to 6.5 to 8.5, with a nitrogen-containing base to form soluble salts of the metals;
   ii) stirring the pH adjusted solution for a time of not less than 15 minutes;
   iii) adjusting the pH of the resulting solution to from 4.5 to 5.5, with an acid, and stirring the resulting solution at a temperature of 75° C. to 85° C. until it is homogeneous;
   iv) preparing an aqueous 0.30 to 0.50 molar solution of vanadyl sulphate at a temperature from room temperature to 80° C.;
   v) mixing the solutions from steps i) or iii) with the solution from step iv) together to provide a molar ratio of V:Mo from 1.00:1 to 1.67:1;
   vi) preparing a solution of $H_2C_2O_4$ and $Nb_2O_5xH_2O$ in a molar ratio from 3:1 to 6.5:1;
   vii) adding the solution from step vi) to the solution of step v) to provide a molar ratio of Mo:Nb from 5.56:1 to 7.14:1 to form a slurry;
   viii) heating the resulting slurry in an autoclave under an inert gas, air, carbon dioxide, carbon monoxide and mixtures thereof at a pressure of not less than 1 psig at a temperature from 140° C. to 190° C. for not less than 6 hours.

2. The process according to claim 1, wherein the temperature for the hydrothermal treatment in step viii) is from 140 0 C to 180*C.

3. The process according to claim 1, wherein the pressure in the autoclave is from 1 to 200 psig.

4. The process according to claim 1, wherein the gaseous product species are vented from the autoclave reactor.

5. The process according to claim 4, wherein there is a condenser upstream of the autoclave outlet.

6. The process according to claim 5, wherein the condenser is operated at a temperature above 0° C. and below reaction temperature.

7. The process according to claim 4, wherein the pressure inside the autoclave is maintained above atmospheric using a liquid filled column or bubbler or pressure regulating device.

8. The process according to claim 1, wherein the time of the hydrothermal treatment in step viii) is from 6 to 60 hours.

9. The process according to claim 1, wherein the aqueous slurry fed to the autoclave comprises Mo, V, Nb and Te salts in a molar ratio; Mo 1; V 0.40 to 0.70; Nb 0.14 to 0.18; and Te 0.14 to 0.20.

10. The process according to claim 9, wherein the heat-treated slurry from step viii) is treated with from 0.3-2.5 mL of a 30 wt. % solution of aqueous $H_2O_2$ per gram of catalyst precursor.

11. The process according to claim 1, wherein the pre-catalyst from step viii) is separated from the aqueous phase and washed with (distilled) water or an aqueous oxalic acid solution and mixtures thereof and dried in an oven for not less than 6 hours at a temperature from 70° C. to 120° C.

12. The process according to claim 11, wherein the dried precatalyst is ground, to a particle size less than 125 μm. The dried catalyst may also be pre-dried in a 90° C. oven for no less than 6 hours before calcination.

13. The process according to claim 12, wherein the dried precatalyst is calcined in an inert atmosphere at a temperature from 200° C. to 650° C. for a time from 1 to 20 hours.

14. The process according to claim 13 where the calcined material is mixed with 0.1 wt. % to 10 wt. % (relative to catalyst) $Nb_2O_5xH_2O$ at 90° C. in water and then dried at 300° C. in air.

15. The process according to claim 14, wherein from 10 wt. % to 95 wt. % of the catalyst is bound or agglomerated with from 5 wt. % to 90 wt. % of a binder selected from the group consisting of acidic, basic or neutral binder slurries of $TiO_2$, $ZrO_2Al_2O_3$, $AlO(OH)$, $Nb_2O_5$, and mixtures thereof provided that $ZrO_2$ is not used in combination with an aluminum containing binder.

16. A method for the oxidative dehydrogenation of a mixed feed comprising ethane and oxygen in a volume ratio from 70:30 to 95:5 and optionally one or more $C_{3-6}$ alkanes or alkenes and oxygenated species including CO and $CO_2$, said method comprising:
   passing said mixture over a catalyst prepared according to claim 1 at a temperature greater than 320° C. and up to 385° C., a gas hourly space velocity of not less than 100 $hr^1$, and a pressure from 0.8 to 7 atmospheres.

17. The method according to claim 16, having a selectivity to ethylene of not less than 90% at a target ethane conversion of greater than 25-35%.

18. The method according to claim 17 wherein the gas hourly space velocity of the ODH process is not less than 500 $hr^{-1}$.

19. The method according to claim 18 wherein the temperature is less than 375° C.

20. The method according to claim 19, wherein the catalyst in the ODH process forms a fixed bed.

* * * * *